United States Patent [19]

Pommer et al.

[11] 4,117,150

[45] Sep. 26, 1978

[54] FURAN DERIVATIVES

[75] Inventors: Ernst-Heinrich Pommer, Limburgerhof; Sabine Thym, Heidelberg-Dossenheim; Wolfgang Reuther, Ziegelhausen, all of Fed. Rep. of Germany

[73] Assignee: BASF Aktiengesellschaft, Ludwigshafen, Fed. Rep. of Germany

[21] Appl. No.: 855,889

[22] Filed: Nov. 30, 1977

[30] Foreign Application Priority Data

Jan. 26, 1977 [DE] Fed. Rep. of Germany ....... 2703023

[51] Int. Cl.$^2$ ...................... A01N 9/12; C07D 307/68

[52] U.S. Cl. .................... 424/285; 260/347.2

[58] Field of Search ..................... 260/347.2; 424/285

[56] References Cited

U.S. PATENT DOCUMENTS

| | | | |
|---|---|---|---|
| 3,959,481 | 5/1976 | Davis et al. | 424/285 |
| 3,978,091 | 8/1976 | Tsuchiya et al. | 260/347.3 |

*Primary Examiner*—Richard L. Raymond
*Attorney, Agent, or Firm*—Keil, Thompson & Shurtleff

[57] ABSTRACT

New and valuable furan derivatives containing a fluorodichloromethylthio radical, fungicides containing these compounds as active ingredients, and processes for combatting fungi with these compounds.

6 Claims, No Drawings

FURAN DERIVATIVES

The present invention relates to new and valuable furan derivatives having a good fungicidal action, methods of manufacturing them, fungicides containing these compounds, and their use as fungicides.

The use of 2,5-dimethylfuran-3-carboxanilide as a fungicide is disclosed in German Pat. No. 1,768,686.

We have now found that furan derivatives of the formula

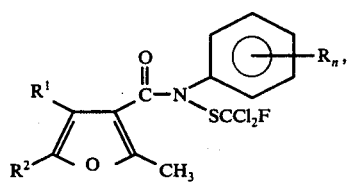

where $R^1$ and $R^2$ are identical or different and each denotes hydrogen or methyl, R denotes halogen (F, Cl, Br, I), $NO_2$, alkyl of from 1 to 4 carbon atoms, substituted alkyl of from 1 to 4 carbon atoms (haloalkyl), alkoxyl of from 1 to 4 carbon atoms, CN, $COOR^3$, alkylthio phenyl or $CF_3$—S—, $R^3$ denoting alkyl of from 1 to 4 carbon atoms, and n denotes one of the integers 0,1 and 2, have a good fungicidal action. They are particularly suitable for use in the protection of materials, e.g., the protection of surface coatings against fungus attack, or of wood against the action of wood-destroying and wood-discoloring fungi. Compared with 2,5-dimethylfuran-3-carboxanilide disclosed in German Pat. No. 1,768,686, the new furan derivatives have a superior action on wood-destroying fungi, e.g., *Merulius lacrimans* and *Polystictus versicolor*, and on the wood-discoloring fungus *Pullularia pullulans*. Additionally, the following fungi may also be controlled: *Coniophora cerebella, Lentinus lepideus, Lenzites trabea, Poria vaporaria, Polystictus versicolor, Fomes annosus, Armillaria mellea, Stereum* spec., *Paecilomyces varotii, Schlerophoma pityophila, Chaetomium globosum, Stemphylium* spec., *Alternaria* spec., and *Botrytis cinerea*. The new compounds are also suitable for combatting fungi in plants.

The new compounds are prepared for example by reaction of a furancarboxanilide of the formula

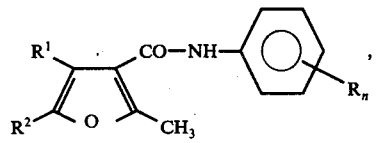

where $R^1$, $R^2$ and $R_n$ have the above meanings, with a fluorodichloromethylsulfenyl chloride of the formula

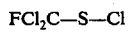

FCl$_2$C—S—Cl at from $-30°$ to $+100°$ C in the presence of an auxiliary base and, if desired, in an organic solvent. This process is preferred.

Examples of suitable auxiliary bases are lithium hydride, sodium hydride, potassium hydride, triethylamine, N-dimethylcyclohexylamine, n-dimethylaniline and n-butyllithium.

Examples of suitable organic solvents are n-pentane, n-hexane, petroleum ether, cyclohexane, benzene, toluene, xylene, chlorobenzene, ether, tetrahydrofuran, dioxane, acetone, diisopropyl ketone, sulfolane, dimethyl sulfoxide, acetonitrile, dimethylformamide, and hexamethylphosphoric acid triamide.

It may at times be advantageous to employ a slight excess of fluorodichloromethylsulfenyl chloride, e.g., from 1.2 to 3.2 moles of chloride per mole of anilide.

However, it is also possible to produce the abovementioned furancarboxanilides from the corresponding acid chloride of the formula

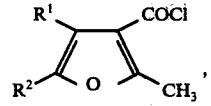

where $R^1$ and $R^2$ have the above meanings, by reaction with an aniline of the formula

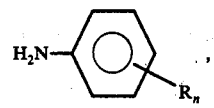

where $R_n$ has the above meanings, and to react them, without previous separation, with fluorodichloromethylsulfenyl chloride in the manner described above. For this reaction, 2 moles of aniline are preferably employed per mole of acid chloride, or the reaction is carried out in the presence of one of the above-mentioned auxiliary bases. It is also possible to prepare a corresponding metal salt from the anilide, e.g., an alkali metal salt and to react it with fluorodichloromethylsulfenyl chloride at from $-30°$ to $+150°$ C, if desired in one of the abovementioned organic solvents.

The preparation of the new furan derivatives is illustrated by the following examples.

EXAMPLE 1

Preparation of the compound

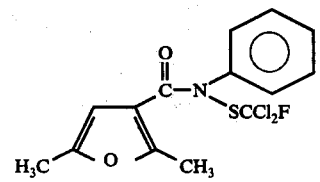

N-(fluorodichloromethylthio)-2,5-dimethylfuran-3-carboxanilide

318 Parts (by weight) of 2,5-dimethylfuran-3-carboxylic acid chloride is placed in 400 parts of toluene. 195 parts of aniline, and 444 parts of triethylamine, in 200 parts of toluene are then dripped in, the temperature rising to 60° C. After 1.5 hours, 357 parts of fluorodichloromethylsulfenyl chloride dissolved in 100 parts of toluene is dripped in. The temperature is allowed to rise to 35° C, and the mixture is stirred for a further 2 hours at room temperature. 34 parts of fluorodichloromethylsulfenyl chloride is added, followed by 30 parts of triethylamine. Stirring is carried out for a further 3 hours at 60° C. After cooling, the precipitated triethylammonium chloride is suction filtered, the filtrate is boiled with animal charcoal and filtered, and the solvent is removed in vacuo. The crude product is recrystallized from n-pentane; yield: 338 parts (m.p.: 58°–60° C). All the other compounds may be prepared analogously.

EXAMPLE 2

Preparation of the compound

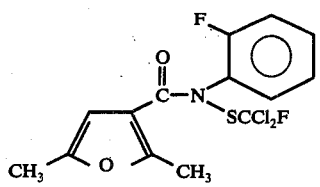

N-(fluorodichloromethylthio)-2,5-dimethylfuran-3-carboxy-2'-fluoroanilide

35 Parts of 2,5-dimethylfuran-3-carboxy-2'-fluoroanilide is refluxed in 150 parts of toluene. A suspension of 6 parts of 80% sodium hydride paste (in white oil) in 40 ml of toluene is added while boiling. After cooling to 0° C, 29 parts of fluorodichloromethylsulfenyl chloride is dripped in. The reaction mixture is poured onto ice and extracted with water, and the precipitation is separated (47.3 parts) and recrystallized from n-pentane; yield: 16.1 parts (m.p.: 44°–45° C).

EXAMPLE 3

Preparation of the compound

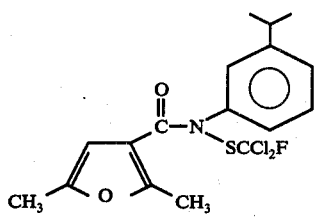

N-(fluorodichloromethylthio)-2,5-dimethylfuran-3-carboxy-3'-isopropylanilide

39 Parts of 2,5-dimethylfuran-3-carboxy-3'-isopropylanilide is refluxed in 150 parts of toluene. A suspension of 6 parts of 80% sodium hydride (remainder:- white oil) in 40 parts of toluene is then added. At 0° C, 29 parts of fluorodichloromethylthiosulfenyl chloride is dripped in. The mixture is then poured onto ice, extracted with water and dried, and the precipitation is separated (56.3 parts). Recrystallization from n-pentane gives a yield of 33 parts (m.p.: 48°–50° C) and from isopropanol/H₂O of 20.7 parts (m.p.: 54°–56° C).

EXAMPLE 4

Preparation of the compound

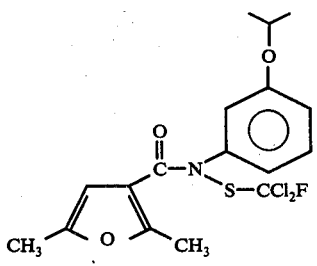

N-(fluorodichloromethylthio)-2,5-dimethylfuran-3-carboxy-3'-isopropoxyanilide 18.4 parts of 2,5-dimethylfuran-3-carboxy-3'-isopropoxyanilide is heated at 100° C in 150 ml of toluene. 2.7 parts of sodium hydride is added and, at from 0° to 5° C, 13.6 parts of fluorodichloromethylsulfenyl chloride in 50 parts of toluene is introduced. After extraction with water and drying, the precipitation is separated (41.7 parts). After recrystallization from n-pentane, there is obtained 13.3 parts of a crystalline mass.

EXAMPLE 5

Preparation of the compound

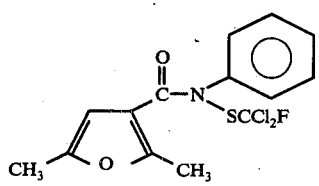

N-(fluorodichloromethylthio)-2,5-dimethylfuran-3-carboxanilide 37.4 Parts (by weight) of fluorodichloromethylsulfenyl chloride, 25 parts of triethylamine and 100 ml of hexane are placed in a reactor. 43 parts of 2,5-dimethylfuran-3-carboxanilide in 20 parts of n-hexane is then added, the temperature rising to 43° C. After stirring for 30 minutes at room temperature (20° C), 7.5 parts of fluorodichloromethylsulfenyl chloride and 5 parts of triethylamine are added, and after 3 hours and at 50° C, another 15 parts of the sulfenyl chloride and 10 parts of triethylamine are added. After the mixture has been stirred for a further hour at 50° C, it is cooled and suction filtered, and the filtrate is boiled with bleaching clay, suction filtered and concentrated. There is obtained 40 g of an oily, crystalline mass.

The precipitate is stirred into water, suction filtered, dried and washed with n-pentane. There is obtained 35 parts of N-(fluorodichloromethylthio)-2,5-dimethylfuran-3-carboxanilide (m.p.: 64°–67° C).

EXAMPLE 6

Preparation of the compound

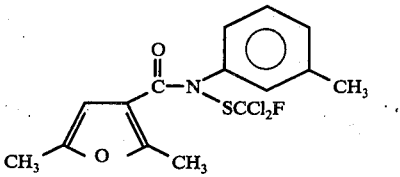

N-(fluorodichloromethylthio)-2,5-dimethylfuran-3-carboxy-3'-methylanilide 27.5 Parts (by weight) of 2,5-dimethylfuran-3-carboxy-3'-methylanilide, 23.8 parts of fluorodichloromethylsulfenyl chloride and 150 ml of toluene are placed in a reactor.

16 Parts of triethylamine is dripped in so slowly as to cause the temperature to rise to 50° C. After cooling, extraction is carried out with water, followed by drying. The product which precipitates out is separated (36.8 parts). After recrystallization from n-hexane with activated carbon, there is obtained 20.4 parts of N-

(fluorodichloromethylthio)-2,5-dimethylfuran-3-carboxy-3'-methylanilide; m.p.: 70°–72° C.

The following compounds may be obtained analogously:

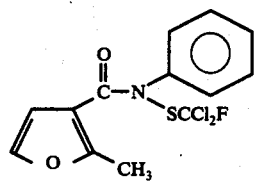

m.p.: 40° C (from pentane)

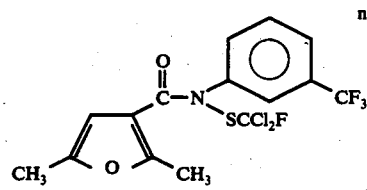

$n_D^{22}$: 1.526

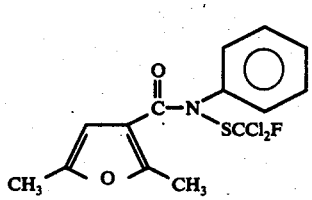

m.p.: 72° to 73° C

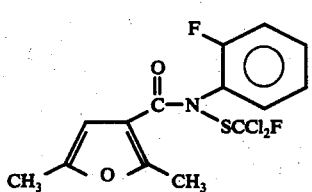

m.p.: 46° to 48° C (from n-pentane)

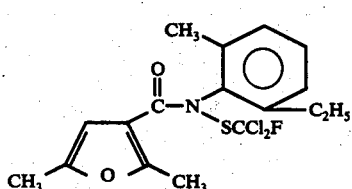

m.p.: 50° to 52° C (from n-pentane)

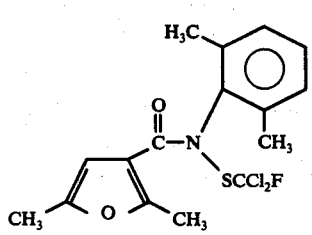

m.p.: 79° to 81° C (from n-pentane)

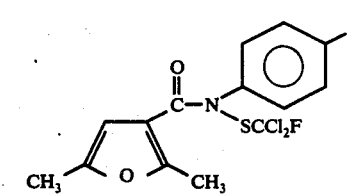

m.p.: 124° to 126° C (from isopropanol)

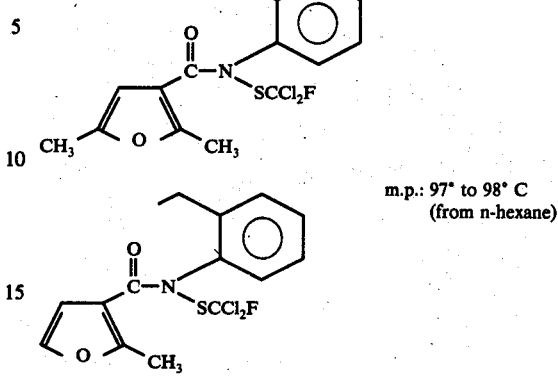

m.p.: 74° to 75° C (from n-pentane)

m.p.: 97° to 98° C (from n-hexane)

The following table contains examples of the new furan derivatives.

| $R^1$ | $R^2$ | R | n | m.p. (° C) |
|---|---|---|---|---|
| H | H | H | 0 | 40 |
| H | H | 2-CH$_3$ | 1 | |
| H | H | 3-CH$_3$ | 1 | |
| H | H | 4-CH$_3$ | 1 | |
| H | H | 2-iC$_3$H$_7$ | 1 | |
| H | H | 3-iC$_3$H$_7$ | 1 | |
| H | H | 4-iC$_3$H$_7$ | 1 | |
| H | H | 3-tC$_4$H$_9$ | 1 | |
| H | H | 4-C$_2$H$_5$ | 1 | |
| H | H | 2-F | 1 | |
| H | H | 3-F | 1 | |
| H | H | 4-F | 1 | |
| H | H | 2-Cl | 1 | |
| H | H | 3-Cl | 1 | |
| H | H | 4-Cl | 1 | |
| H | H | 2-Br | 1 | |
| H | H | 3-Br | 1 | |
| H | H | 4-Br | 1 | |
| H | H | 4-I | 1 | |
| H | H | 3-CF$_3$ | 1 | |
| H | H | 4-CF$_3$ | 1 | |
| H | H | 3-NO$_2$ | 1 | |
| H | H | 4-NO$_2$ | 1 | |
| H | H | 2,6-CH$_3$ | 2 | |
| H | H | 2-CH$_3$, 6-C$_2$H$_5$ | 2 | |
| H | H | 2-CH$_3$, 6-iC$_3$H$_7$ | 2 | |
| H | H | 2-CH$_3$, 5-NO$_2$ | 2 | |
| H | H | 2,3-CH$_3$ | 2 | |
| H | H | 3-O-iC$_3$H$_7$ | 1 | |
| H | H | 3,5-Cl | 2 | |
| H | H | 2,6-Cl | 2 | |
| H | H | 3,5-CF$_3$ | 2 | |
| CH$_3$ | H | H | 0 | |
| CH$_3$ | H | 2-F | 1 | |
| CH$_3$ | H | 4-F | 1 | |
| CH$_3$ | H | 2-Cl | 1 | |
| CH$_3$ | H | 3-Cl | 1 | |
| CH$_3$ | H | 4-Cl | 1 | |
| CH$_3$ | H | 3-Br | 1 | |
| CH$_3$ | H | 4-I | 1 | |
| CH$_3$ | H | 3-CF$_3$ | 1 | |
| CH$_3$ | H | 3-iC$_3$H$_7$ | 1 | |
| CH$_3$ | H | 3-O-iC$_3$H$_7$ | 1 | |
| CH$_3$ | H | 3-NO$_2$ | 1 | |
| CH$_3$ | H | 3-NO$_2$,6-CH$_3$ | 2 | |
| CH$_3$ | H | 2-Cl, 6-Cl | 2 | |
| H | CH$_3$ | H | 0 | 72–73 |
| H | CH$_3$ | 2-F | 1 | 46–48 |
| H | CH$_3$ | 3-F | 1 | 55–61 |
| H | CH$_3$ | 4-F | 1 | 62–64 |
| H | CH$_3$ | 2-Cl | 1 | 87–89 |
| H | CH$_3$ | 3-Cl | 1 | 74–75 |

-continued

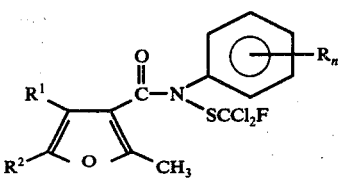

| $R^1$ | $R^2$ | R | n | m.p. (° C) |
|---|---|---|---|---|
| H | CH₃ | 4-Cl | 1 | 70-71 |
| H | CH₃ | 2-Br | 1 | 100-102 |
| H | CH₃ | 3-Br | 1 | 53-55 |
| H | CH₃ | 4-Br | 1 | 85-86 |
| H | CH₃ | 4-I | 1 | 124-126 |
| H | CH₃ | 3-CF₃ | 1 | $n_D^{25}$: 1.526 |
| H | CH₃ | 3-COiC₃H₇ | 1 | 69-71 |
| H | CH₃ | 2-NO₂ | 1 | $n_D^{25}$: 1.5519 |
| H | CH₃ | 3-NO₂ | 1 | $n_D^{25}$: 1.5732 |
| H | CH₃ | 4-NO₂ | 1 | 98-100 |
| H | CH₃ | 2-CH₃ | 1 | 84-85 |
| H | CH₃ | 3-CH₃ | 1 | 70-72 |
| H | CH₃ | 4-CH₃ | 1 | 74-75 |
| H | CH₃ | 4-C₂H₅ | 1 | 68-69 |
| H | CH₃ | 2-C₂H₅ | 1 | 97-98 |
| H | CH₃ | 3-C₂H₅ | 1 | |
| H | CH₃ | 2-n-C₃H₇ | 1 | |
| H | CH₃ | 3-n-C₃H₇ | 1 | |
| H | CH₃ | 2-i-C₃H₇ | 1 | 74-75 |
| H | CH₃ | 3-i-C₃H₇ | 1 | 54-56 |
| H | CH₃ | 4-i-C₃H₇ | 1 | 73-75 |
| H | CH₃ | 4-C₆H₅ | 1 | 97-99 |
| H | CH₃ | 3-C—O—i-C₃H₇ (‖ O) | 1 | |
| H | CH₃ | 3-sec-C₄H₉ | 1 | |
| H | CH₃ | 3-O-i-C₃H₇ | 1 | crystalline mass |
| H | CH₃ | 3-O-n-C₃H₇ | 1 | |
| H | CH₃ | 3-O-t-C₄H₉ | 1 | |
| H | CH₃ | 3-O-sec-C₄H₉ | 1 | |
| H | CH₃ | 3-O-n-C₄H₉ | 1 | |
| H | CH₃ | 3-O—CF₃ | 1 | |
| H | CH₃ | 4-O—CF₃ | 1 | |
| H | CH₃ | 3-C—O—i-C₃H₇ (‖ O) | 1 | |
| H | CH₃ | 4-SCF₃ | 1 | |
| H | CH₃ | 2-NO₂ | 1 | |
| H | CH₃ | 4-CH₃, 3-NO₂ | 2 | 94-95 |
| H | CH₃ | 2-CH₃, 5-NO₂ | 2 | 100-102 |
| H | CH₃ | 2,3-CH₃ | 2 | 92-93 |
| H | CH₃ | 2,6-CH₃ | 2 | 79-81 |
| H | CH₃ | 2-CH₃-6-C₂H₅ | 2 | 50-52 |
| H | CH₃ | 2,6-F | 2 | |
| H | CH₃ | 2,6-Cl | 2 | |
| H | CH₃ | 3,5-Cl | 2 | 56-58 |
| H | CH₃ | 3,4-F | 2 | |
| H | CH₃ | 3-F, 4-Cl | 2 | |
| H | CH₃ | 3-Cl, 4-F | 2 | |
| H | CH₃ | 2-Cl, 5-NO₂ | 2 | |
| H | CH₃ | 2-Cl, 4-NO₂ | 2 | |
| H | CH₃ | 3,5-CF₃ | 2 | |
| H | CH₃ | 3,4-Cl | 2 | |
| H | CH₃ | 2,4-Cl | 2 | |
| H | CH₃ | 2,5-Cl | 2 | |
| CH₃ | CH₃ | H | 0 | 78-79 |
| CH₃ | CH₃ | 2-F | 1 | 65-67 |
| CH₃ | CH₃ | 3-F | 1 | 67-68 |
| CH₃ | CH₃ | 4-F | 1 | 78-80 |
| CH₃ | CH₃ | 2-i-C₃H₇ | 1 | oil |
| CH₃ | CH₃ | 2-i-C₃H₇ | 1 | oil |
| CH₃ | CH₃ | 3-NO₂ | 1 | |
| CH₃ | CH₃ | 4-NO₂ | 1 | |
| CH₃ | CH₃ | 3-CF₃ | 1 | |
| CH₃ | CH₃ | 4-C₂H₅ | 1 | |
| CH₃ | CH₃ | 2-CH₃, 5-NO₂ | 2 | |
| CH₃ | CH₃ | 3,5-Cl | 2 | |
| CH₃ | CH₃ | 2,6-CH₃ | 2 | |
| CH₃ | CH₃ | 3,4-F | 2 | |
| CH₃ | CH₃ | 3-Cl, 4-F | 2 | |
| CH₃ | CH₃ | 4-CF₃, 3-Cl | 2 | |

The new furan derivatives are preferably used as fungicidally active components of oily wood preservatives. They are applied by treating the wood with them, for instance by impregnation or coating. Application rates are from 0.5 to 10 kg of active ingredient per m³ of wood. The concentration of impregnation solutions is from 0.1 to 10 wt% of active ingredient, preferably from 1 to 2 wt %; oily wood preservatives applied by coating methods at rates of from 100 to 250 g/m² of wood surface preferably contain from 1 to 5% of active ingredient.

Due to their excellent fungicidal properties, the new furan derivatives may also be used for protecting materials, e.g., for preserving technical products, as additives to surface coating compositions to prevent fungus attack, or in the crop protection field to combat phytopathogenic fungi such as *Botrytis cinerea* in strawberries, grapes or pimientos.

The fungicides according to the invention may also be applied together with other active ingredients, e.g., insecticides, termiticides and fungicides. When the fungicides of the invention are admixed with other fungicides, the spectrum of fungicidal action is often increased; with some mixtures, synergistic effects also occur, i.e., the fungicidal action of the combination product is greater than that of the individual components when added together.

Examples of suitable fungicides for such combinations are as follows: pentachlorophenol and its salts, organotin compounds, such as tributyltin oxide, copper naphthenate, chloronaphthalene, metal salts of N-nitroso-N-cyclohexylhydroxylamine, 2-methoxycarbonylaminobenzimidazole, N-fluorodichloromethylthiophthalimide, and N,N-dimethyl-N'-phenyl-(N'-fluorodichloromethylthio)-sulfamide.

In the examples which follow, the active ingredients in the table below were used.

| Compound | $R^1$ | $R^2$ | R | n |
|---|---|---|---|---|
| 1 | H | CH₃ | H | 0 |
| 2 | H | CH₃ | 2-CH₃ | 1 |
| 3 | H | CH₃ | 3-CH₃ | 1 |
| 4 | H | CH₃ | 4-CH₃ | 1 |
| 5 | H | CH₃ | 2,6-CH₃ | 2 |
| 6 | H | CH₃ | 2,3-CH₃ | 2 |
| 7 | H | CH₃ | 2-CH₃,6-C₂H₅ | 2 |
| 8 | H | CH₃ | 3-i-C₃H₇ | 1 |
| 9 | H | CH₃ | 4-i-C₃H₇ | 1 |
| 10 | H | CH₃ | 3-t-C₄H₉ | 1 |
| 11 | H | CH₃ | 2-F | 1 |
| 12 | H | CH₃ | 3-F | 1 |
| 13 | H | CH₃ | 4-F | 1 |
| 14 | H | CH₃ | 3,5-Cl | 2 |
| 15 | H | CH₃ | 3-NO₂ | 1 |
| 16 | CH₃ | CH₃ | H | 0 |
| 17 | CH₃ | CH₃ | 2-F | 1 |
| 18 | CH₃ | CH₃ | 4-F | 1 |

EXAMPLE 7

Disc-shaped filter papers having a diameter of 13 mm and a thickness of 1 mm are impregnated with 0.2 ml solutions containing 200, 100, 50 or 25 parts of active ingredient per million parts of solution (ppm). The discs are then placed on a 5% malt extract agar in Petri dishes which have been centrally inoculated with the mycelium of the wood-destroying fungi *Merulius lacrimans* and *Polystictus (Coriolus) versicolor*. The dishes are then incubated for 3 days at from 22° to 24° C. After this period, the fungi in the control dishes are well developed; the fungicidal action of the active ingredients is assessed from the fungus-free zones (halos) which have formed round the paper discs, as follows:

− no halo = no fungicidal action
+ small halo < 1 mm = slight fungicidal action
++ average halo 1–5 mm = good fungicidal action
+++ large halo > 5 mm = excellent fungicidal action.

| Active ingredient | ppm active ingredient in solution | | | |
|---|---|---|---|---|
| | 200 | 100 | 50 | 25 |
| a) Merulius lacrimans | | | | |
| 1 | +++ | +++ | +++ | +++ |
| 2 | +++ | +++ | +++ | +++ |
| 3 | +++ | +++ | +++ | ++ |
| 4 | +++ | +++ | ++ | ++ |
| 5 | +++ | +++ | ++ | ++ |
| 6 | +++ | +++ | +++ | +++ |
| 7 | +++ | +++ | +++ | ++ |
| 8 | +++ | +++ | +++ | +++ |
| 9 | +++ | ++ | ++ | + |
| 10 | +++ | +++ | +++ | +++ |
| 11 | +++ | +++ | +++ | +++ |
| 12 | +++ | +++ | ++ | − |
| 13 | +++ | +++ | +++ | +++ |
| 14 | +++ | +++ | ++ | ++ |
| 15 | ++ | ++ | ++ | ++ |
| 16 | +++ | +++ | ++ | ++ |
| 17 | +++ | +++ | +++ | +++ |
| 18 | +++ | +++ | +++ | ++ |
| (German 1,768,686) | +++ | ++ | − | − |
| Control (no active ingredient) | − | | | |
| b) Polystictus versicolor | | | | |
| 1 | +++ | +++ | +++ | +++ |
| 2 | ++ | ++ | − | − |
| 3 | ++ | ++ | − | − |
| 6 | ++ | + | + | + |
| 8 | +++ | ++ | − | − |
| 10 | ++ | − | − | − |
| 11 | +++ | ++ | − | − |
| 12 | ++ | + | − | − |
| 13 | +++ | ++ | − | − |
| 16 | ++ | + | − | − |
| (German 1,768,686) | + | − | − | − |
| Control (no active ingredient) | − | | | |

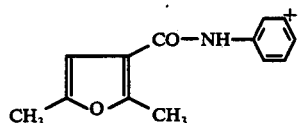

EXAMPLE 8

To prepare an oily wood preservative containing 0.5% of active ingredient, 0.5 part of active ingredient no. 1 is first dissolved in 55 parts of a gasoline fraction rich in aromatics. Subsequently, 10 parts of an alkyd resin is added and the mixture made up to 100 parts with white spirit. Oily wood preservatives containing 1 and 2% and more active ingredient are prepared analogously.

A waterproofing effect may be obtained by adding water repellents to the oily wood preservative. Examples of suitable substances are zinc stearate, aluminum stearate and waxes. Color effects may also be obtained by incorporating inorganic or organic pigments. The excellent fungicidal action of the fungicides according to the invention is apparent from the following example.

The test for determining the resistance to wood-destroying fungi was carried out in accordance with German standard DIN 52,176 ("Examination of wood preservatives—short-term mycological test—block method"). The test fungus was Coniophora cerebella. Pine sapwood blocks measuring 50×25×15 mm were coated with solutions of the oily wood preservatives (100 ml/m² wood surface). After an evaporation period of 4 weeks, the blocks were placed in glass dishes infested with Coniophora cerebella. The experiment was carried out over a 16-week period, after which the loss in weight of the blocks caused by destruction of the wood was determined and compared with untreated control blocks.

| Oily wood preservative Active ingredient | Amount added in % | % loss in weight after 16 weeks |
|---|---|---|
| 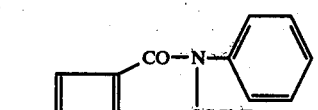 | 0.5 | less than 2 |
| | 1.0 | 0 |
| | 2.0 | 0 |
| Control (untreated) | − | 27 |

EXAMPLE 9

Pimiento seedlings of the "Neusiedler Ideal Elite" variety were sprayed, after 4 to 5 leaves were well developed, to runoff with 0.1 wt% aqueous liquors containing (dry basis) 80% of active ingredient and 20% of sodium lignin sulfonate. After the sprayed-on layer had dried, the plants were sprinkled with a conidial suspension of the fungus Botrytis cinerea, and placed at 22° to 24° C in a chamber of high humidity to obtain optimum conditions for promoting fungus growth. After 5 days, the disease had spread to such a great extent on the untreated plants that the necroses covered the major portion of the leaves.

| Active ingredient | Leaf necroses after spraying with 0.1% liquor |
|---|---|
| 1 | 0 |
| 16 | 0 |
| 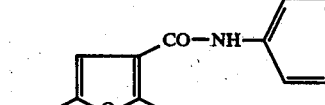 | 4 |
| (German 1,768,686) Control (untreated) | 5 |

0 = no necrose, graduated down to
5 = ⅓ of leaf surface covered with necroses

EXAMPLE 10

90 Parts by weight of compound 1 is mixed with 10 parts by weight of N-methyl-α-pyrrolidone. A mixture is obtained which is suitable for application in the form of very fine drops.

EXAMPLE 11

20 Parts by weight of compound 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 12

20 Parts by weight of compound 3 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 13

20 Parts by weight of compound 1 is dissolved in a mixture consisting of 25 parts by weight of cyclohexanol, 65 parts by weight of a mineral oil fraction having a boiling point between 210° and 280° C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 14

20 Parts by weight of compound 2 is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 15

3 Parts by weight of compound 3 is intimately mixed with 97 parts by weight of particulate kaolin. A dust is obtained containing 3% by weight of the active ingredient.

EXAMPLE 16

30 Parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 17

40 Parts by weight of compound 1 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt% of active ingredient.

EXAMPLE 18

20 Parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

Application may be effected for instance in the form of directly sprayable solutions, powders, suspensions, dispersions, emulsions, oil dispersions, pastes, dusts, broadcasting agents, or granules by spraying atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations for crop protection contain from 0.1 to 95, and preferably 0.5 to 90, % by weight of active ingredient.

We claim:

1. A furan derivative of the formula

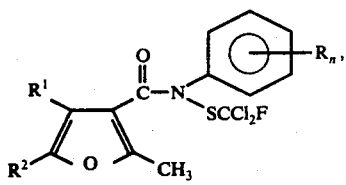

where $R^1$ and $R^2$ are identical or different and each denotes hydrogen or methyl, R denotes halogen, $NO_2$, alkyl of from 1 to 4 carbon atoms, haloalkyl of from 1 to 4 carbon atoms, alkoxyl of from 1 to 4 carbon atoms, CN, $COOR^3$, alkylthio, phenyl or $CF_3$—S—, $R^3$ denoting alkyl of from 1 to 4 carbon atoms, and n denotes one of the integers 0, 1 and 2.

2. A process for the protection of wood against wood-destroying and wood-discoloring fungi, wherein the wood is treated with a fungicidally effective amount of a furan derivative of the formula

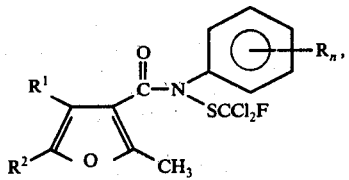

where $R^1$ and $R^2$ are identical or different and each denotes hydrogen or methyl, R denotes halogen, $NO_2$, alkyl of from 1 to 4 carbon atoms, haloalkyl of from 1 to 4 carbon atoms, alkoxyl of from 1 to 4 carbon atoms, CN, $COOR^3$, alkylthio, phenyl or $CF_3$—S—, $R^3$ denoting alkyl of from 1 to 4 carbon atoms, and n denotes one of the integers 0, 1 and 2.

3. N-(fluorodichloromethylthio-)2,4-dimethylfuran-3-carboxanilide.

4. N-(fluorodichloromethylthio-)-2-methylfuran-3-carboxanilide.

5. N-(fluorodichloromethylthio-)2,5-dimethylfuran-3-carboxanilide.

6. N-(fluorodichloromethylthio-)2,4,5-trimethylfuran-3-carboxanilide.

* * * * *